United States Patent [19]

Shih et al.

[11] Patent Number: 4,699,784

[45] Date of Patent: Oct. 13, 1987

[54] TUMORICIDAL METHOTREXATE-ANTIBODY CONJUGATE

[75] Inventors: Lisa B. Shih, Cedar Grove; Frederick J. Primus, Pittstown; Milton D. Goldenberg, Short Hills, all of N.J.

[73] Assignee: Center for Molecular Medicine & Immunology, Newark, N.J.

[21] Appl. No.: 833,204

[22] Filed: Feb. 25, 1986

[51] Int. Cl.[4] .................. A61K 31/705; A61K 37/44; C07K 15/00

[52] U.S. Cl. ..................................... 424/85; 530/391; 530/809

[58] Field of Search ................... 530/391, 809; 424/85

[56] References Cited

U.S. PATENT DOCUMENTS 4,046,722  9/1977  Rowland .......................... 530/391 X
4,093,607  6/1978  Sela et al. ....................... 530/391 X
4,263,279  4/1981  Sela et al. ............................... 424/85
4,315,851  2/1982  Yoshikumi et al. ................. 530/391

FOREIGN PATENT DOCUMENTS 0038695  9/1983  European Pat. Off. .

OTHER PUBLICATIONS

Int. J. Cancer, 13: 151–163 (1974), Banjo et al.
Europ. J. Cancer, 13 (1977), 593–596, Rowland.
J. Natl. Cancer Inst., 61, (1978), 657–676, Ghose et al.
Cancer Research, 41, 2700–2706, (1981), Kulkarni et al.

*Primary Examiner*—Howard E. Schain
*Attorney, Agent, or Firm*—Bernhard D. Saxe

[57] ABSTRACT

A conjugate of methotrexate to an antibody is prepared by loading methotrexate onto an aminodextran, then specifically conjugating the polymer carrier to the carbohydrate portion of an antitumor antibody, using a reduced Schiff base linkage. The conjugate is useful for tumor targeted therapy.

12 Claims, No Drawings

TUMORICIDAL METHOTREXATE-ANTIBODY CONJUGATE

BACKGROUND OF THE INVENTION

The present invention relates to a conjugate of methotrexate to an antibody, in which the methotrexate is first loaded onto an aminodextran and this intermediate is in turn site-specifically conjugated to an antitumor antibody. The resultant conjugate targets the methotrexate cytotoxicity to a tumor cell for a therapeutic result.

Conjugation of cytotoxic drugs to antibodies to achieve a targeted therapeutic result is known. In particular, it is known that methotrexate (MTX) can be conjugated to antibodies and some selective cytotoxicity has been observed. It is desirable to enhance the selectivity and cytotoxicity of such conjugates by increasing the antibody loading of the cytotoxic drug. However, multiple conjugation of individual drug molecules to an antibody eventually reduces its immunoreactivity, the effect being observed when more than about 10 drug molecules are loaded.

It has been suggested that the drug be conjugated to an intermediate polymeric carrier, which in turn would be conjugated to antibody. This has the advantage that larger numbers of drug molecules can be attached to the antibody at fewer sites on the antibody itself, so that immunoreactivity is not as seriously compromised.

One approach has been to attach MTX to bovine serum albumin (BSA) and then randomly link the intermediate to antibody, as reported by Garrett et al., Int. J. Cancer, 31: 661–670, 1983. These authors were able to attach about 37 MTX molecules to BSA (average molecular weight of 70,000) but the resultant antibody conjugate had an immunoreactivity of only about 28% of that of the intact antibody.

Use of polylysine as a polymer carrier was reported by Ryser et al., Proc. Natl. Acad. Sci. USA, 75: 3867–3870, 1978. These authors found that only about 13 MTX per carrier could be loaded and immunoreactivity was poor. In addition, the high amine content of the polymer, largely in the form of charged ammonium groups, caused the conjugate to stick to normal cells and vitiated the selectivity of the cytotoxic effect.

A need therefore continues to exist for an antibody conjugate of MTX that combines high loading with minimal decrease in immunoreactivity for selective targeting of MTX to tumor cells.

OBJECTS OF THE INVENTION

One object of the present invention is to provide a conjugate of MTX to an anticancer antibody wherein many MTX molecules are attached to the antibody for enhanced tumoricidal effect.

Another object of the invention is to provide a conjugate of MTX to an anticancer antibody wherein the conjugate has substantially the same immunoreactivity as intact antibody.

Another object of the present invention is to provide a conjugate of MTX to an anticancer antibody wherein the conjugate does not appreciably bind to non-target tumor cells and wherein the targeted conjugate can enter the tumor cell and achieve its tumoricidal effect therein.

Another object of the invention is to provide a conjugate of MTX to an anticancer antibody wherein the conjugate has improved circulation half-life in blood.

Another object of the invention is to provide a method of producing a MTX-antibody conjugate having the aforementioned properties.

Another object of the present invention is to provide a method of tumor therapy using the foregoing MTX-antibody conjugate for targeted drug delivery.

Upon further study of the specification and appended claims, further objects and advantages of this invention will become apparent to those skilled in the art.

SUMMARY OF THE INVENTION

These objects can be attained by providing an antibody conjugate, comprising methotrexate linked through one of its carboxyl groups to an aminodextran polymer, which in turn is linked through at least one of its amino groups to the carbohydrate portion of an anti-cancer antibody by a reduced Schiff base linkage.

The invention further includes a method of preparing a methotrexate-aminodextran-antibody conjugate, comprising the steps of:

(a) reacting an aminodextran containing about 25–50 methotrexate molecules linked thereto with an anti-cancer antibody having an oxidized carbohydrate portion; and (b) reductively stabilizing the resultant Schiff base adduct.

Also included in the invention is a method of tumor therapy, comprising administering to an animal or human having a tumor a therapeutically effective amount of an antibody conjugate, comprising methotrexate linked through one of its carboxyl groups to an aminodextran polymer, which in turn is linked through at least one of its amino groups to the carbohydrate portion of an anti-cancer antibody by a reduced Schiff base linkage.

DETAILED DISCUSSION

The general method of preparing a methotrexate-aminodextran-antibody conjugate (MTX-AD-Ab) according to the invention involves reacting an anti-cancer antibody whose carbohydrate portion has been oxidized with a MTX-AD intermediate having residual free amino groups. This results in an initial Schiff base (imine) linkage, which is stabilized by reduction to a secondary amine to form the final conjugate.

The process normally starts with a dextran polymer, advantageously a dextran of average molecular weight (MW) of about 10,000–100,000, preferably about 30,000–60,000, and more preferably about 40,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably about 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less than desirable loading of MTX.

The oxidized dextran is then reacted with a polyamine, preferably a diamine, and more preferably a mono- or polyhydroxy diamine. Suitable such amines include, e.g., ethylene diamine, propylene diamine or other like polymethylene diamine, diethylene triamine or like polyamines, 1,3-diamino-2-hydroxypropane or other like hydroxylated diamine or polyamine, and the like. Earlier workers have generally used ethylene diamine, but the present inventors have shown that better results are achieved with a solubilizing diamine such as 1,3-diamino-2-hydroxypropane. An excess of the amine relative to the aldehyde groups is used, to insure substantially complete conversion of the aldehyde functions to Schiff base (imine) groups.

Reductive stabilization of the resultant intermediate is effected by reacting the Schiff base intermediate with a reducing agent. e.g., $NaBH_4$, $NaBH_3CN$ or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the number of available primary amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

The AD is then reacted with a carboxyl-activated MTX to form a MTX-AD intermediate adduct. Activation of MTX is conveniently effected with any of the conventional carboxyl-activating reagents, e.g., dicyclyhexylcarbodiimide (DCC) or the like, optionally followed by reaction with N-hydroxysuccinimide (HOSu), to form the active ester. The reaction is normally effected in a polar, aprotic solvent, e.g., dimethylformamide (DMF), dimethylsulfoxide (DMSO) or the like. Other activated esters, e.g., p-nitrobenzoate and the like, can also be used, as can mixed anhydrides. The DCC/HOSu activation is mild and the activated MTX can be reacted in aqueous medium with the AD, so it is preferred.

The proportions of activated MTX to AD are preferably such that about half of the amino groups available on the AD react to form amide bonds with the carboxyl of the activated MTX. Thus, if about 100 amine groups are available on an AD with a starting MW of about 40,000, up to about 50 of these should be reacted with activated MTX. Using a proportion of about 50:1 MTX:AD, about 25–50 MTX molecules are normally introduced. It is difficult to achieve higher loading because of incipient precipitation of the adduct due to the increasing insolubility thereof.

The MTX-AD adduct can be conjugated to any antibody which specifically binds to an antigen produced by or associated with a tumor which is responsive to methotrexate therapy. Examples of such antigens are human chorionic gonadotropin (HCG), carcinoembryonic antigen (CEA), alpha-fetoprotein (AFP), breast gross cystic disease protein, breast epithelial cell antigen, and other breast, lung, ovarian, germ cell, brain, lymphoma and leukemia antigens. Antibodies to such antigens can be developed by immunizing a suitable animal host with purified anti-cancer antigens or tumor or normal organ/tissue extracts and/or cells.

These antigens and/or cells/extracts can also be used in conventional methods of producing hybridomas which produce monoclonal antibodies. Human or primate hybridoma monoclonal antibodies can be produced by a combination of genetic engineering and hybridoma technology.

The next step involves oxidation of the carbohydrate portion of the antibody chosen for the conjugate. This is conveniently effected either chemically, e.g., with $NaIO_4$ or other glycolytic reagent, or enzymatically, e.g., with neuraminidase and galactose oxidase. The latter is a convenient method which is well known for linking amino moieties to antibodies, e.g., as reported by Banjo et al., Int. J. Cancer, 13:151–163, 1974.

The proportion of oxidized antibody and MTX-AD adduct are adjusted so that an average of about 1–3 adducts are linked to the antibody. This will result in a MW for the conjugate of less than about 300,000, which is desirable to promote adequate loading without interfering with cellular uptake and diffusion into solid tumor, and at the same time avoiding or at least mitigating rapid clearance of the conjugate from the blood stream. Attachment of the MTX-AD conjugate to the antibody in a site-specific manner on the carbohydrate portion of the molecule preserves the antibody binding activity, while at the same time permitting a high loading of the drug.

Administration of the MTX-AD-Ab can be effected in a variety of ways depending upon the type and location of the tumor to be treated. For example, administration can be intravenous, intraarterial, intraperitoneal, intrapleural, intrathecal, subcutaneous, by perfusion through a regional catheter, or by direct intralesional injection.

The conjugate will generally be administered as a sterile aqueous solution in phosphate-buffered saline. Dosage units of about 10–200 mg of conjugate will be administered, normally daily for a period of several days. It may be necessary to reduce the dosage and/or use antibodies from other species and/or hypoallergenic antibodies, e.g., hybride human or primate antibodies, to reduce patient sensitivity.

Intravenous, intraarterial or intrapleural administration is normally used for lung, breast, and leukemic tumors. Intraperitoneal administration is advised for ovarian tumors. Intrathecal administration is advised for brain tumors and leukemia. Subcutaneous administration is advised for Hodgkin's disease, lymphoma and breast carcinoma. Catheter perfusion is useful for metastatic lung, breast or germ cell carcinomas of the liver. Intralesional administration is useful for lung and breast lesions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of amino dextran

One gram of dextran (MW 40,000, Sigma) is partially oxidized by $NaIO_4$ (0.33 g) in aqueous solution to form polyaldehyde dextran. The mixture is stirred in the dark for 1 hr at room temperature. The solution is concentrated by amicon cell (YM10 membrane MWCO=10,000) and purified by Sephadex G-25 column. The material is lyophilized to give 898 mg of white powder (89.8% yield).

The polyaldehyde dextran (800 mg, 0.02 mmole) is dissolved in 80 ml H$_2$O and then reacted with 1,3-diamino-2-hydroxypropane (200 mg, 2.15 mmole) at room temperature for 24 hours. Sodium borohydride (11.8 mg, 0.311 mmole) is added and reacted at room temperature for 2 hours. The material is membrane filtered through YM-10 and XM-50 to eliminate the small molecules, and at the same time control the molecule weight at the selected ranges.

The level of the amino groups is assayed by TNBS (trinitrobenzene-sulfonic acid) using glucosamine as the reference material. The NH$_2$ level is found to be 100/dextran.

EXAMPLE 2

Preparation of Methotrexate/aminodextran intermediate (a) Activation of Methotrexate In a dried Reacti-vial, 45.4 mg of methotrexate (0.1 mmole, Sigma) in 1 ml anhydrous DMF is introduced by syringe. A solution of N-hydroxysuccinimide (23 mg, 0.2 mmole, Sigma) in 7590 ul of anh. DMF and a solution of 1,3-dicyclohexylcarbodiimide (41.5 mg, 0.2 mmole, Sigma) in 750 ul of anh. DMF are followed. The reaction mixture is stirred in the dark at room temperature for 16 hours under anhydrous conditions. The white precipitate is centrifuged and the clear solution is stored in a sealed bottle at $-20°$ C.

(b) Reaction with Aminodextran

Aminodextran (10 mg, 2.5×10$^{-4}$ mmole) is dissolved in 2 ml of PBS, pH 7.2. Activated MTX (125×10$^{-4}$ mmole) is added gradually. The solution is stirred at room temperature for 5 hours and purified by Sephadex G-25 column. The void volume is collected and further dialyzed against reaction buffer. After lyophilization, 2.1 mg of product is obtained (21% yield). The methotrexate incorporation is determined by the absorption at 370 nm (=6500) to be 38 Methotrexate/dextran.

EXAMPLE 3

Preparation of antibody conjugate (a) Oxidation of Antibody

Anti-CEA monoclonal antibody is selectively oxidized by sodium metaperiodate to form aldehyde groups on the carbohydrate moiety. The procedure is as follows: Antibody (2 mg/ml) in PBS, pH 7.2 is reacted with 20 ul of sodium metaperiodate (2.84 ng/ml) in the dark at room temperature for 90 minutes. Ethylene glycol (2 ul) is then added. After 15 minutes, the oxidized antibody is purified by Sephadex G-25 column. The IgG fraction is collected and condensed to approximately 1 ml and used in the following conjugation.

(b) Conjugation

The oxidized antibody (about 2 mg) is reacted with methotrexate/aminodextran intermediate prepared according to Example 2 (2.5 mg, 62.5×10$^{-6}$ mmole) in PBS, pH 7.2. The solution is reacted at 4° C. for 48 hours. The resultant Schiff base is stabilized by sodium cyanoborohydride (10-fold excess over the antibody). After sizing chromatography on Sephacryl S-300, the conjugate appears as a symmetrical peak and is collected. The protein concentration is determined by Lowry assay to be 1.05 mg (52.5% yield). The concentration of methotrexate is determined by the absorption at 370 nm (=6500). The conjugate is found to contain 91 molecules of methotrexate per IgG molecule, which indicates that at least two dextran bridges are attached to the antibody.

The immunoreactivity of the conjugate is studied by flow-cytometry using indirect fluorescence label technique. The data are compared with unmodified antibody and show that the conjugation by this method does not alter the immunoreactivity of the antibody.

EXAMPLE 4

LS174T (colon adenocarcinoma) cells are treated with trypsin/EDTA, washed with complete media (RPMI-1640, 10% FCS, 1000 u/ml penicillin, 1000 ug/ml streptomycin, 25 mM Hepes), and added to microtiter well strips at 4×10 cells/well in 100 ul, 6 replicates for each treatment. After 4 hrs, 37° C., 6% CO$_2$, antibody-methotrexate conjugates are added along with the appropriate controls (free MTX, free MTX+free antibody). The cells are incubated for an additional 24 hours 37° C., 6% CO$_2$, at which time 0.1 uCi of 75-Se-selenomethionine is added for 16–18 hrs. Plates are washed 4 times. Individual wells are separated and counted in a gamma counter. The conjugate at a dose of about 3 uM causes about 50% of cell mortality.

EXAMPLE 5

Tumor Therapy

A female patient having a small-cell carcinoma diffusely metastasized in both lobes of the lung is treated by intravenous injection of a solution of 100 mg of MTX-AD-anti-CEA antibody conjugate in PBS, at a concentration of 10 mg/ml. The treatment is repeated for five successive days. CAT scans prior to treatment and 30 days after the last administration of the conjugate demonstrate 60% reduction in tumor volume.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An antibody conjugate, comprising methotrexate linked through one of its carboxyl groups to an aminodextran polymer, which in turn is linked through at least one of its amino groups to the carbohydrate portion of an anti-cancer antibody by a reduced Schiff base linkage.

2. The antibody conjugate of claim 1, wherein said anti-cancer antibody specifically binds to an antigen produced by or associated with a lung, breast or epidermoid tumor.

3. The antibody conjugate of claim 2, wherein said antigen is carcinoembryonic antigen.

4. The antibody conjugate of claim 3, wherein said antibody is a monoclonal antibody.

5. The antibody conjugate of claim 1, wherein said aminodextran has about 50–150 amino groups thereon.

6. The antibody conjugate of claim 5, wherein said aminodextran is a condensation product of dextran and 1,3-diamino-2-hydroxypropane.

7. The antibody conjugate of claim 5, wherein said conjugate has about 25-50 methotrexate molecules per aminodextran.

8. The antibody conjugate of claim 5, wherein said conjugate has 1-3 methotrexate-aminodextran moieties per antibody.

9. A method of preparing a methotrexate-aminodextran-antibody conjugate wherein the methotrexate is linked through one of its carboxyl groups to an aminodextran polymer, which in turn is linked through at least one of its amino groups to the carbohydrate portion of an anti-cancer antibody by a Reduced Schiff base linkage, comprising the steps of:

(a) reacting an aminodextran containing about 25-40 methotrexate molecules linked thereto with an anti-cancer antibody having an oxidized carbohydrate portion; and (b) reductively stabilizing the resultant Schiff base adduct.

10. The method of claim 9, wherein said methotrexate-loaded aminodextran used in step (a) is produced by reacting carboxylactivated methotrexate with aminodextran.

11. The method of claim 9, wherein said aminodextran is a condensation product of dextran and 1,3-diamino-2-hydroxypropane.

12. A method of tumor therapy, comprising administering to an animal or human having a tumor a therapeutically effective amount of an antibody conjugate, comprising methotrexate linked through one of its carboxyl groups to an aminodextran polymer, which in turn is linked through at least one of its amino groups to the carbohydrate portion of an anti-cancer antibody by a reduced Schiff base linkage.

* * * * *

UNITED STATES PATENT AND TRADEMARK OFFICE
CERTIFICATE OF CORRECTION

| | |
|---|---|
| PATENT NO. | : 4,699,784 |
| DATED | : October 13, 1987 |
| INVENTOR(S) | : Lisa B. Shih et al. |

It is certified that error appears in the above-identified patent and that said Letters Patent is hereby corrected as shown below:

Column 1,
After the title, please insert:

-- GOVERNMENT LICENSE RIGHTS

The U.S. Government has a paid-up license in this invention and the right in limited circumstances to require the patent owner to license others on reasonable terms as provided for by the terms of grant number CA 39841-02, awarded by the National Institutes of Health. --

Signed and Sealed this

Twenty-third Day of October, 2001

*Attest:*

NICHOLAS P. GODICI
*Acting Director of the United States Patent and Trademark Office*

*Attesting Officer*